United States Patent [19]

Hoffmeister

[11] 4,011,873
[45] Mar. 15, 1977

[54] SURGICAL INSTRUMENT FOR LIGATURES
[76] Inventor: Axel Hoffmeister, Kantstr. 13, 68 Mannheim, 1, Germany
[22] Filed: July 11, 1975
[21] Appl. No.: 595,011
[30] Foreign Application Priority Data
July 13, 1974 Germany .................. 7423891[U]
[52] U.S. Cl. .................. 128/326; 128/340; 242/137.1
[51] Int. Cl.² .................. A61B 17/12; A61B 17/06
[58] Field of Search ............ 128/326, 334 R, 339, 128/340; 223/103, 104; 242/137.1

[56] References Cited
UNITED STATES PATENTS

| 373,372 | 11/1887 | King | 128/340 |
| 891,358 | 6/1908 | Morgan | 223/104 |
| 2,008,251 | 7/1935 | Hillebrand | 128/339 |
| 2,092,929 | 9/1937 | Ovington | 128/339 X |
| 3,545,658 | 12/1970 | Tanemura | 223/104 |

Primary Examiner—Channing L. Pace
Attorney, Agent, or Firm—Staas & Halsey

[57] ABSTRACT

A surgical instrument for ligatures is disclosed herein consisting of a hollow handle in the inside of which thread spools are mounted rotatably, the hollow handle extending into a tube, the lower end of which has a curved portion which ends in a point, a flattened portion provided in the area of curvature, and exit openings for the unwound threads provided on both sides behind the point of the instrument.

3 Claims, 5 Drawing Figures

U.S. Patent
Mar. 15, 1977
4,011,873
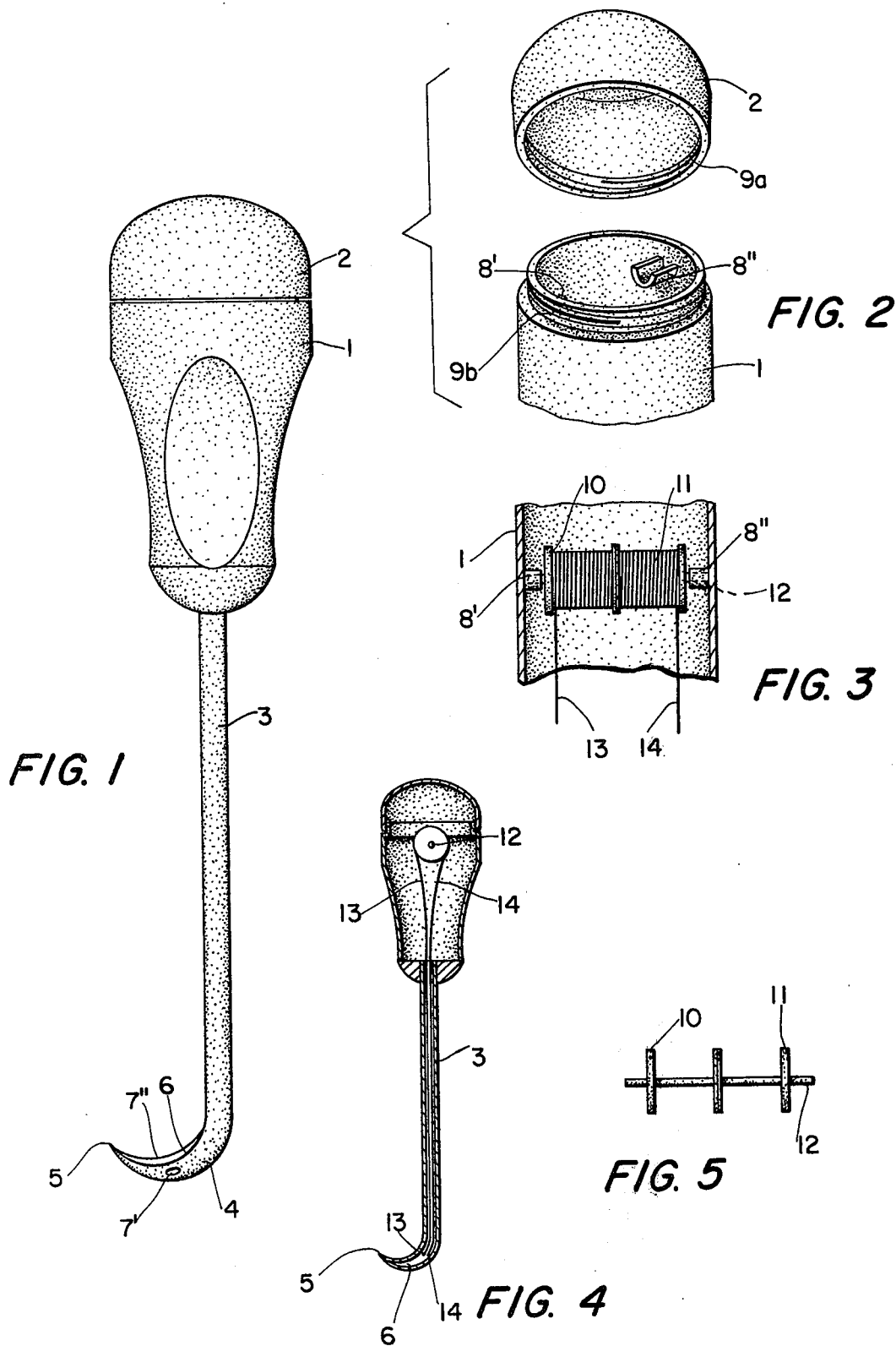

SURGICAL INSTRUMENT FOR LIGATURES

BACKGROUND AND SUMMARY OF THE INVENTION

The present innovation relates to a surgical instrument with which particularly ligatures can be carried out quickly and securely.

For the ligature and the subsequent separation of tissue which has numerous vessels, for example, in the case of maceration of parts of the stomach and/or intestines in abdomen surgery, at the present time two instruments are still generally required, namely, the so-called groove and thread holder.

Using these two instruments, the ligature operation begins with the fact that the surgeon accepts the groove and pierces the tissue that is to be ligatured; then a thread is introduced through the eye of the thread holder; subsequently, the surgeon accepts the thread holder and guides the latter in the recess of the groove through the tissue. Then a thread is guided for a second time through the eye of the thread holder; then the thread holder is accepted by the surgeon and the thread holder is guided in the recess of the groove through the tissue. Subsequently the two introduced threads are knotted and finally the tissue located between the two ligatures is distinctly separated. In the case of the use of the groove and thread holder, previously described, uncontrolled bleedings in tissues rich in vessels is avoided, as would develop in the case of ligatures with a needle, since the groove has a blunt point. However, this method of operation is still relatively cumbersome because it uses two instruments.

The novel surgical instrument disclosed herein makes possible the carrying out of this ligature operation in an essentially simpler manner, whereby one instrument according to the innovation disclosed herein is required.

The device according to the present invention consists of a hollow handle in which two spools for threads are disposed rotatably followed by a slender tube which is bent at the lower end and which forms a point, whereby the slender tube is developed flat within the range of this bend and has exit openings for the two threads in the range of bending always laterally behind the point. Preferably, the two spools of thread lie on a joint horizontal axle, which on its part is mounted in the legs of a half tube with blue steel clamps.

BRIEF DESCRIPTION OF THE DRAWINGS:

FIG. 1 is a side view of the instrument according to the present invention;

FIG. 2 is a perspective view of the upper part of the hollow handle;

FIG. 3 is a sectional view showing the two thread spools;

FIG. 4 is a sectional view through the surgical instrument according to the present invention; and FIG. 5 is an elevational view of the double thread spool in a joint horizontal axis.

DESCRIPTION OF THE PREFERRED EMBODIMENT:

The reference number 1 designates the hollow handle which has a cap 2 that can be screwed on; at the lower end of the hollow handle the thin tube 3 is disposed perpendicularly, and has at its end the bent range 4 with point 5. This bent range has a flattened portion 6 in the form of a cylindrical surface, it being understood that the surface is not limited to a circular cylinder; on the two sides of the bent area there are openings 7' and 7" which serve as the points of exit for the two threads.

In FIG. 2, the legs 8' and 8" of the half tube are illustrated. These legs serve as bearings for the axle of the thread spools; the reference number 9a designates the inside thread of the cap 2 while the reference numeral 9b designates the corresponding outside thread of the hollow handle 1.

The mounting of the two thread spools 10 and 11, which are independent of one another, is shown in FIG. 3 wherein it will be seen that the joint axle 12 rests in the half pipe legs 8' and 8", whereby mounting support with blue steel clamps can be provided. The thread 13 is wound onto spool 10 and the thread 14 onto spool 11.

From FIG. 4, which represents a perpendicular cut through the surgical instrument according to the innovation, whereby this cut is turned by 90° as compared to the presentation of the cut of FIG. 3, it can be seen how the two spools are unwound contra rotatingly such that the two threads 13 and 14 will always leave the hollow handle downwards on separate sides in relation to the joint axle 12, how they run through the thin tube 3 and finally emerge to the outside through the two opposite openings in the range behind point 5 and are available for the above shown surgery.

In FIG. 5, the joint axle 12 is shown with the two thread spools 10 and 11, which are independent of one another.

The threads to be used commercially are available in sizes and types in the form of so-called throw away spools which have been packaged in a sterile manner.

In the case of the surgical instrument according to the invention, the various thread spools can be charged with differently colored threads and/or with threads of variable quality or dimensioning.

I claim:

1. A surgical instrument for ligatures, comprising:
    a handle provided with an opening therein, a rod, means removable mounting said rod in said handle, two spools, and means mounting said spools on said rod for independent rotation with respect to each other, and
    a tube having a first open end attached to said handle so as to provide communication between said handle and said tube and a second closed end, a curved portion intermediate said ends of said tube, the outer surface of said tube at the inner portion of said curve having a cylindrical surface and two openings provided in said curved portion of said tube and positioned diametrically to each other.

2. A surgical instrument as in claim 1, further comprising one continuous length of thread provided on each of said two spools and wherein said two openings are arranged in said curved portions of said tube so as to allow two separate and non-intersecting paths to be defined by said two lengths of thread as each of said length passes from the interior of said handle through the interior of said tube and then through one of said two openings, respectively.

3. A surgical instrument as in claim 2, further comprising a cap which covers said opening in said handle and means for removably mounting said cap on said handle and wherein said spools are alternately arranged on said rod so that said spools turn counter rotatingly with respect to each other when said threads are unwound therefrom.

* * * * *